(12) United States Patent
Mech et al.

(10) Patent No.: US 9,095,722 B2
(45) Date of Patent: Aug. 4, 2015

(54) MICRO-MINIATURE IMPLANTABLE COATED DEVICE

(75) Inventors: Brian Mech, Stevenson Ranch, CA (US); Robert J. Greenberg, Los Angeles, CA (US); Honggang Jiang, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1235 days.

(21) Appl. No.: 11/343,170

(22) Filed: Jan. 30, 2006

(65) Prior Publication Data

US 2006/0173497 A1    Aug. 3, 2006

Related U.S. Application Data

(60) Provisional application No. 60/649,816, filed on Feb. 1, 2005.

(51) Int. Cl.
*A61N 1/372* (2006.01)
*A61N 1/375* (2006.01)
*A61N 1/05* (2006.01)

(52) U.S. Cl.
CPC .............. *A61N 1/372* (2013.01); *A61N 1/375* (2013.01); *A61N 1/05* (2013.01); *A61N 1/37205* (2013.01)

(58) Field of Classification Search
CPC . A61N 1/0472; A61N 1/303; A61N 1/36125; A61N 1/37205; A61N 1/3758
USPC ............... 600/373, 377, 381; 607/2, 115, 116
See application file for complete search history.

(56) References Cited

U.S. PATENT DOCUMENTS

| 4,996,629 | A | | 2/1991 | Christiansen et al. |
| 5,405,367 | A | * | 4/1995 | Schulman et al. ............... 607/61 |
| 6,051,017 | A | * | 4/2000 | Loeb et al. ......................... 607/1 |
| 6,389,317 | B1 | * | 5/2002 | Chow et al. ...................... 607/54 |
| 6,411,854 | B1 | * | 6/2002 | Tziviskos et al. ............... 607/57 |
| 6,718,628 | B2 | * | 4/2004 | Munshi ............................ 29/825 |
| 6,844,023 | B2 | * | 1/2005 | Schulman et al. ........... 427/2.24 |

(Continued)

FOREIGN PATENT DOCUMENTS

| WO | WO 02/102267 A1 | 12/2002 |
| WO | WO 2004/014479 A2 | 2/2004 |

OTHER PUBLICATIONS

Hirvonen, James K.; Ion Beam Assisted Thin Film Deposition; Materials Science Reports 6; 1991; 215-274; Elsevier Science Publishers B.V. (North Holland).

(Continued)

*Primary Examiner* — Christopher D Koharski
*Assistant Examiner* — Frances Oropeza
(74) *Attorney, Agent, or Firm* — Scott B. Dunbar; Gary Schnittgrund; Tomas Lendvai

(57) ABSTRACT

An implantable micro-miniature device is disclosed. The device comprises a thin hermetic insulating coating and at least one thin polymer or metal secondary coating over the hermetic insulating layer in order to protect the insulating layer from the erosive action of body fluids or the like. In one embodiment the insulating layer is ion beam assisted deposited (IBAD) alumina and the secondary coating is a parylene polymer. The device may be a small electronic device such as a silicon integrated circuit chip. The thickness of the insulating layer may be ten microns or less and the thickness of the secondary layer may be between about 0.1 and about 15 microns.

23 Claims, 3 Drawing Sheets

(56) References Cited

U.S. PATENT DOCUMENTS

| | | | |
|---|---|---|---|
| 6,926,670 B2 * | 8/2005 | Rich et al. | 600/459 |
| 7,039,465 B2 * | 5/2006 | Bardy et al. | 607/36 |
| 7,054,692 B1 * | 5/2006 | Whitehurst et al. | 607/149 |
| 7,169,106 B2 * | 1/2007 | Fleischman et al. | 600/399 |
| 7,455,667 B2 * | 11/2008 | Uhland et al. | 604/890.1 |
| 7,565,203 B2 * | 7/2009 | Greenberg et al. | 607/54 |
| 7,684,868 B2 * | 3/2010 | Tai et al. | 607/54 |
| 2002/0119176 A1 | 8/2002 | Greenberg et al. | |
| 2003/0040781 A1 * | 2/2003 | Larson et al. | 607/36 |
| 2003/0080085 A1 * | 5/2003 | Greenberg et al. | 216/20 |
| 2003/0109903 A1 | 6/2003 | Berrang et al. | |

OTHER PUBLICATIONS

Smidt, F.A.; Use of Ion Beam Assisted Deposition to Modify the Microstructure and Properties of Thin Films; International Materials Reviews; 1990; 61-128, vol. 35, No. 2; The Institute of Metals and ASM International.

* cited by examiner

| SAMPLE | TEST PROCEDURE AND DAYS | AREA I INTERFACE | AREA II SUBMERGED | AREA III ABOVE INTERFACE |
|---|---|---|---|---|
| #1 IBAD ALUMINA + PRIME + PARYLENE | FULLY SOAKED 236 DAYS | NO PARYLENE PEEL-OFF, COATING (ALUMINA + PARYLENE) INTACT | | |
| #2 IBAD ALUMINA + PARYLENE | FULLY SOAKED 236 DAYS | VERY SMALL AREA PARYLENE PEEL-OFF, MOST AREA COATINGS (ALUMINA + PARYLENE) INTACT | | |
| #3 IBAD ALUMINA ONLY | FULLY SOAKED 236 DAYS | ALUMINA COATING STILL THERE, BUT WITH DEGRADATION | | |
| #4 IBAD ALUMINA ONLY | HALF SOAKED 120 DAYS | ALUMINA COATING GONE | WHITISH ALUMINA COATING DEGRADED | SHINY ALUMINA INTACT |
| #5 IBAD ALUMINA + PARYLENE | HALF SOAKED 120 DAYS | MAJOR AREA: ALUMINA + PARYLENE; MINOR AREA: COATING GONE | ALUMINA + PARYLENE INTACT | PARYLENE GONE, ALUMINA INTACT |
| #6 IBAD ALUMINA + PRIME + PARYLENE | HALF SOAKED 120 DAYS | MAJOR AREA: ALUMINA + PARYLENE; MINOR AREA: COATING GONE | ALUMINA + PARYLENE INTACT | PARYLENE + ALUMINA INTACT EXCEPT ONE SPOT |

TABLE 1. POST-SALINE SOAKED CHIP
(57° C, PASSIVE SOAK, PHOSPHATE-BUFFERED SALINE)

*Fig. 4*

MICRO-MINIATURE IMPLANTABLE COATED DEVICE

CROSS-REFERENCE TO RELATED APPLICATIONS

This application claims hereby the benefit of Provisional Patent Application No. 60/649,816, entitled "Silicon Implant With Coated IBAD Alumina", filed Feb. 1, 2005, the disclosure of which is hereby incorporated by reference.

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to implantable medical devices and components, and is particular related to coatings for micro-miniature implantable devices.

BACKGROUND OF THE INVENTION

Biocompatibility is a critical concern for medical devices that are designed to be implanted in vivo. Biocompatibility is necessary to avoid adverse reactions in the subject, and to avoid device failure as a result of exposure to the corrosive saline body fluids and other substances in the tissue surrounding the implant. Where an implanted device includes one or more components that are not, themselves, biocompatible, it is known to provide hermetic sealing of such devices with a chemically inert coating to achieve biocompatibility, i.e., in order to avoid adverse reactions and device degradation. Many such implantable devices are intended to remain in place over long periods of time, imposing a long life requirement on the hermetic sealing.

Large implantable electronic devices, such as pacemakers, are typically enclosed within a hermetic case. Size and thickness is not critical to such devices and so it is relatively easy to provide hermetic encasement. However, micro-miniature implantable devices, which commonly include microelectronic components such as integrated circuit chips fabricated on silicon substrates, are generally not encased and instead, use relatively thin layers of a deposited hermetic material for sealing. Such micro-miniature devices include, for example, implantable nerve stimulators such as visual prostheses, cochlear prostheses, deep brain stimulators, spinal chord stimulators, and functional electrical stimulators for motor control. In the case of micro-miniature implantable medical devices, biocompatible and electrically insulating metal oxide films have been deposited on the surface of components, such as integrated circuits, passive electronic devices and components, magnets, and mechanical pieces, in order to passivate them and make them less susceptible to attack in the body. These are referred to as "hermetic coatings", where the word hermetic is used to mean that the films do not leak significantly, and thus prevent fluids, and materials in the fluids, from reaching the components to be protected.

Ion beam assisted deposition ("IBAD") of ceramic materials such as alumina, (often referred to an aluminum oxide ($Al_2O_3$)), has been used for hermetically sealing micro-miniature devices. Alumina has good biocompatibility, and IBAD is a useful technique for depositing dense, adherent, defect-free conformal thin films. The use of IBAD to deposit alumina on implantable medical devices is described in U.S. Pat. No. 6,844,023, entitled "Alumina Insulation For Coating Implantable Components And Other Microminiature Devices," the disclosure of which is incorporated by reference. IBAD may be used to deposit electrical insulators on integrated circuits, passive components, magnets, and other implantable devices in order to provide a thin, hermetically sealed package. Typically, layers deposited using IBAD are only a few microns thick.

The inventors have found that a thin insulating layer, such as alumina deposited by IBAD, may not provide adequate long-term protection of implantable devices. Specifically, the inventors have determined that such layers are subject to erosion in the body and are, therefore, susceptible to failure over time. Some metal oxides, such as alumina, although generally considered to be inert, undergo slow reactions in the presence of water. Whether the reactions are due to aqueous chemistry, the presence of ions in solution, the presence of atomic oxygen, or some other mechanisms or combinations of mechanisms, the resulting reactions produce changes in the surface of the metal oxide and a slow, persistent thinning of the insulating layer. Where the insulating is a thin film that was deposited to protect a device, the resulting erosion of this film compromises the functional utility of the film. Thus, the utility of known hermetic coatings for micro-miniature devices is jeopardized by the reactive processes that eventually result in the failure of the thin insulating coating.

In order to use thin hermetic insulating films as protective coatings for micro-miniature implantable devices intended for long-term use, a way of extending their lifetime is required. One possible way to extend the lifetime of the insulating coating is to increase the thickness of the deposited film. However, this approach is often incompatible with the intrinsic stress of the film which tends to build with increasing thickness, ultimately causing the film to crack. Even if the problem of stress could be overcome, the slow growth rate of such films (e.g., 1-2 Angstrom/sec), makes the growth of thick films unattractive from a manufacturing perspective, and so an alternative to merely increasing the thickness of the insulating layer is desirable.

SUMMARY OF THE INVENTION

It is an object of the invention to provide an implantable device employing an electrically insulating hermetic layer that is protected from dissolution by a protective polymer or metal coating.

Other objects, advantages and novel features of the present invention will become apparent from the following detailed description of the invention when considered in conjunction with the accompanying drawing.

In one embodiment, the present invention is directed to a micro-miniature implantable device comprising, a device for use within a living organism, a biocompatible inorganic hermetic insulating layer covering said device, and a biocompatible protective polymer layer overlying said insulating layer. The device may comprise an active electronic circuit, such as an integrated circuit chip, or a passive component such as a resistor, inductor, capacitor or magnet. In one embodiment, the inorganic hermetic layer comprises a ceramic layer, such as a metal oxide layer, for example, aluminum oxide ($Al_2O_3$), zirconium oxide ($ZrO_2$), titanium dioxide ($TiO_2$), vanadium oxide ($V_2O_5$) or suitable mixtures thereof. Alternatively, the insulating layer comprises silicon carbide (SiC), titanium nitride (TiN), aluminum nitride (AlN), silicon nitride ($Si_3N_4$), silicon dioxide ($SiO_2$) or ultra-nano crystalline diamond, or suitable mixtures thereof. In a preferred embodiment the polymer is parylene. Other suitable polymers comprise polyimides, silicones, an epoxies, liquid crystal polymers, polyethylene glycols, polyethylene terephthalates tetrafluoroethylenes, or suitable mixtures thereof. The hermetic insulating layer is preferably less than about 10 microns thick. The polymer layer is preferably less than about 15 microns thick and, more preferably between about 3 and about 15 microns thick, and more preferably between about 4 and about 10 microns thick. In another embodiment, a second biocompatible protective layer is formed over the polymer layer.

Another embodiment of the present invention is directed to a micro-miniature implantable device comprising a device for use within a living organism, a biocompatible inorganic hermetic insulating layer covering said device, and an outer biocompatible metal layer overlying said insulating layer. The metal layer preferably comprises gold, titanium, platinum, iridium or mixtures thereof, and may be preferably between about 0.01 and about 10 microns thick, more preferably between about 0.02 and about 8 microns thick, and even more preferably between about 0.03 and about 6 microns thick. In a preferred embodiment, the metal layer is titanium.

In another aspect, the present invention is directed to a method of making a micro-miniature implantable device, comprising, providing a micro-miniature device, coating a least a major portion of the device with a thin insulating hermetic layer, and coating the insulating layer with a biocompatible polymer and/or metal layer.

BRIEF DESCRIPTION OF THE DRAWINGS

The foregoing aspects and the attendant advantages of this invention will become more readily apparent by reference to the following detailed description when taken in conjunction with the accompanying drawings, wherein:

FIG. 4 is a table showing experimental results obtained by testing erosion of coatings on micro-miniature devices.

DETAILED DESCRIPTION

The novel features of the invention are set forth with particularity in the appended claims. The invention will be best understood from the following description when read in conjunction with the accompanying drawings. In general, the present invention is directed to an implantable micro-miniature device, and method of manufacture, that has improved hermetic properties.

There are many emerging and potential applications for very small implantable devices, and often keeping the size of the device to a minimum is critical for such applications. Such devices include, for example, implantable nerve stimulators including visual prostheses, cochlear prostheses, deep brain stimulators, spinal chord stimulators, and functional electrical stimulators for motor control. Micro-miniature implantable devices, especially electronic devices comprising integrated circuit chips, must be well protected from the corrosive and other hostile effects of in vivo implantation. However, prior art device encasement techniques, such as employed with pacemakers, are too bulky for practical use in micro-miniature implantable devices. IBAD has proven to be one effective technique in preparing hermetic insulating films with thicknesses of a few microns. Other deposition and coating techniques, although not presently preferred, can also produce suitable hermetic films, especially when used in connection with the present invention. For example, microwave enhanced chemical vapor deposition is a preferred technique for depositing insulating layers of ultra-nano crystalline diamond.

Figure 1:
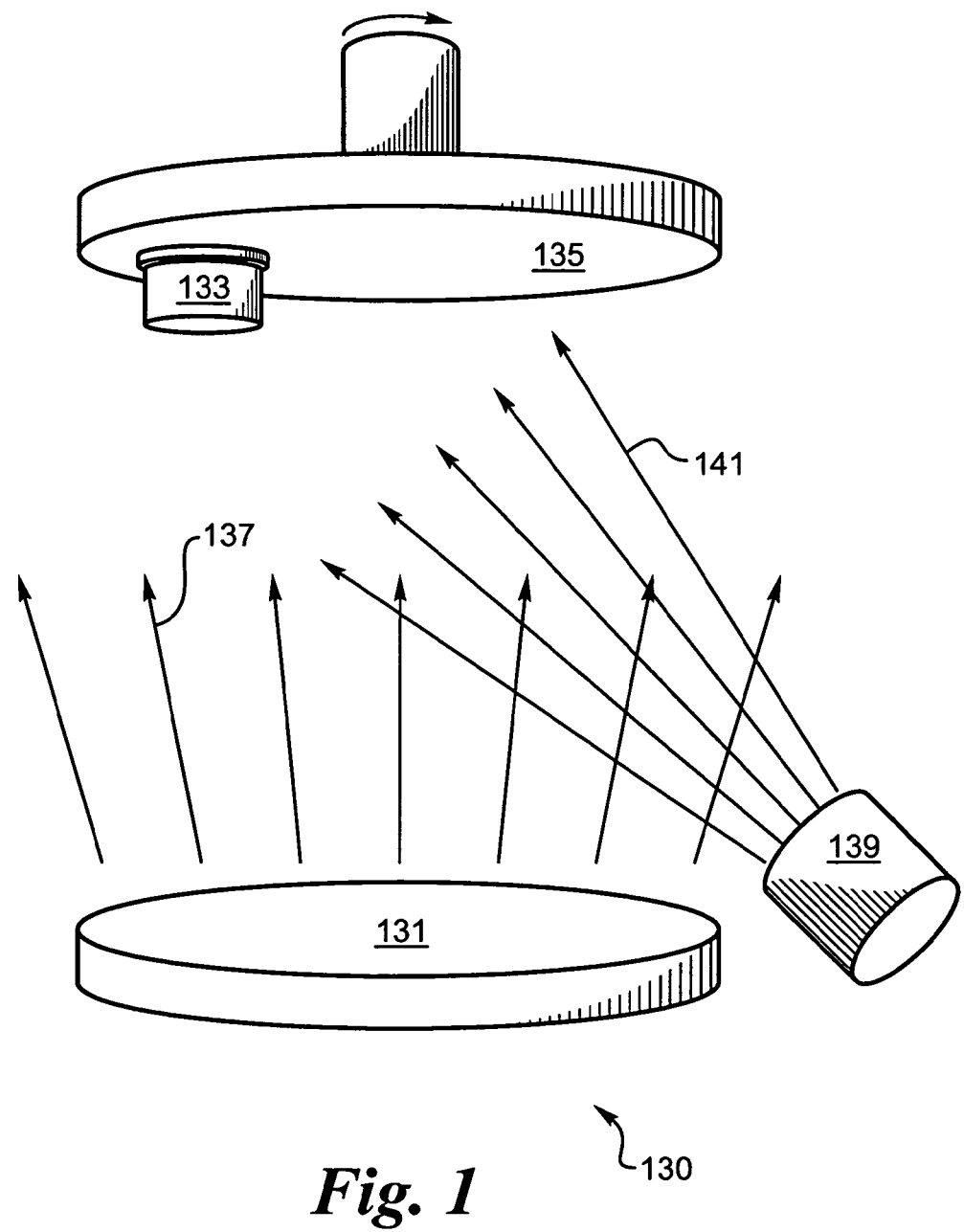
FIG. 1 schematically depicts an ion beam assisted deposition process.

The present invention utilizes one or more thin hermetic coatings of a biocompatible inorganic insulating material, such as metal oxide ceramic materials, e.g., alumina. Such insulating materials may be deposited by any suitable technique. Presently preferred is an ion-beam assisted deposition (IBAD) technique, as generally illustrated in FIG. 1, because they are currently understood to produce the most dense and defect free films. IBAD coatings of non-conductive materials also offer electrically insulating characteristics in salt water, for example, of less than about $10^{-6}$ amps/cm$^2$ of leakage current. IBAD ceramic insulating coatings can also be patterned by conventional techniques. IBAD is a line-of-sight deposition process that achieves very dense coatings in a cost-affordable process.

As noted, the inventors have observed that alumina thin films deposited on silicon substrates by IBAD degrade over time when placed in an aqueous or saline solution. Experiments have shown that degradation rates are on the order of two microns per year or less at body temperature. Furthermore, this degradation is exacerbated by the presence of a liquid/air interface, suggesting that oxygen and/or hydrogen may play a role in the degradation. It has been observed in controlled experiments that when the passivation samples are fully submerged in a defined volume of liquid, the degradation proceeds to a point of saturation and then stops, presumably because the supply of reactants has been consumed. However, this saturation-limiting effect would not apply to most in vivo environments, where the supply of surrounding body fluids is naturally replenished.

According to the present invention, a secondary coating or coatings is applied to the thin insulating coating in order to extend the life of the insulating coating. Specifically, the present invention comprises the application of a thin polymer or metal coating to the insulating layer which protects the insulating layer from this destructive dissolution. In a preferred embodiment, a thin parylene polymer layer is applied over the insulating layer by vacuum vapor deposition.

Figure 2:
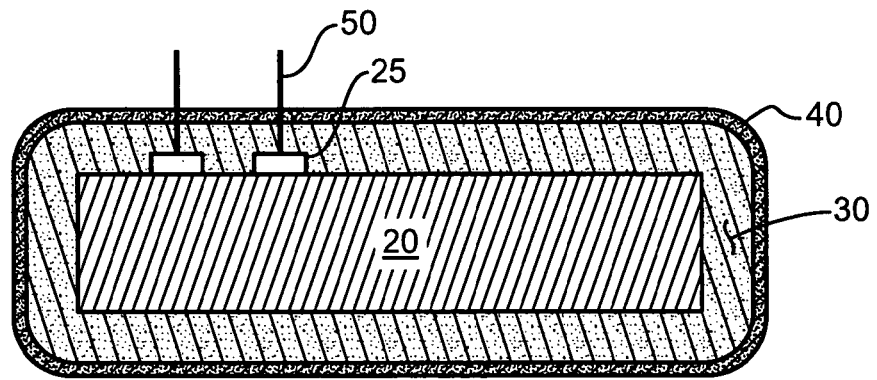
FIG. 2 is a cross-sectional drawing of an implantable micro-miniature device in accordance with an embodiment of the present invention.

FIG. 2 depicts a micro-miniature device 10, in accordance with an exemplary embodiment of the present invention. Device 10 comprises an integrated circuit ("IC") chip 20 having a plurality of contact pads 25. IC chip 20 may be fabricated on a silicon substrate using conventional semiconductor processing technology. Surrounding IC chip 20 is a thin, conformal hermetic coating of an inorganic insulating material 30. Surrounding insulating material 30 is a thin, conformal polymer or metal coating 40. Wires 50 extend through the coatings, allowing external connection to contact pads 25 on IC chip 20. Inorganic hermetic insulating layer 30 is preferably about ten microns thick or less.

As described above, insulating material 30 is preferably deposited by ion beam assisted deposition (IBAD). The insulating material is preferably a biocompatible ceramic material, more preferably a metal oxide. While alumina has been mentioned, and is presently preferred, other biocompatible metal oxides, including zirconia, yttria-stabilized zirconia, titania or vanadia can also be used. Moreover, rather than using a metal oxide, other inert inorganic compounds may be used, including, for example, silicon carbide, titanium nitride, aluminum nitride, silicon nitride, silicon dioxide or ultra-nano crystalline diamond. Preferably whatever inorganic insulating coating is used is substantially impermeable and hermetic at a thickness at approximately 10 microns or less.

FIG. 1 shows an IBAD process using deposition apparatus 130. IBAD is a vacuum-deposition process that combines physical vapor deposition and ion beam bombardment to achieve a highly dense, pin-hole free coating. The electron-beam evaporator 131 generates a vapor of coating atoms 137 which are deposited on a substrate 133. The substrate 133 is mounted on a rotating substrate holder 135 to assure that the coating is applied uniformly to the substrate 133. A distinguishing feature of IBAD is that the coating is bombarded with energetic ions 141 as it is being deposited on the substrate 133. The energetic ions are generated by the ion source 139. IBAD coatings of alumina or other ceramic materials are presently preferred over other known deposition techniques because they can be substantially impermeable in coatings as thin as 10 microns, are stronger than other vapor deposited coatings, and have better adhesion. IBAD is a relatively low temperature process, which can be critical for devices that cannot be processed at high temperature. Since IBAD is a line-of-sight process, it generally will be necessary to coat device 20 from multiple angles to ensure that all of the surfaces are coated.

According to the present invention the lifetime of insulating layer 30 is extended by applying a secondary coating or layer 40 comprising a polymer or thin metal that prevents or reduces the rate of dissolution of insulating layer 30. According to the present invention it is not necessary that layer 40 be hermetic.

Layer 40 provides an extra thickness of material which serves as an initial barrier to fluids which attack insulating layer 30. Moreover, as noted, IBAD is a relatively slow deposition process which is limited by stress in the deposited films. Polymer or metal coating 40 can be is deposited at a much higher rate without excessive stress in the layer, and without affecting the stress of the underlying insulating layer. Moreover, since the insulating layer provides adequate hermetic sealing, it is relatively unimportant if coating 40 is susceptible to degradation itself.

According to the present invention, coating 40 either sufficiently slows or substantially completely stops the erosive processes that cause degradation of the insulating layer 30. For example, if the small but finite concentration of oxygen in solution is causing dissolution of an alumina coating, the presence of a polymeric coating on top of the alumina slows or prevents this, since the oxygen would have an affinity for attachment to the polymer.

Thus, for an insulating layer 30 of given thickness, say 10 microns, the lifetime of an implantable device can be substantially extended using this invention. Conversely, for a given predetermined lifetime, a thinner layer of insulating material 30 could be employed than would otherwise be necessary. Each of these options represent a significant manufacturing advantage.

As noted, according to the present invention, layer 40 can be either a biocompatible polymer or a biocompatible metal layer. Such layers can be applied to the surface of insulating layer 30 by a variety of means. Biocompatible metals include gold, titanium, platinum and iridium and suitable mixtures thereof. Methods for depositing thin layers of these metals are well known, and include various physical or chemical vapor deposition techniques such as e-beam evaporation, sputtering, molecular beam epitaxy, plasma enhanced chemical vapor deposition, etc. According to the present invention, the metal layer is preferably between about 0.01 and about 10 microns thick, more preferably between about 0.02 and about 8 microns thick, and even more preferably between about 0.03 and about 6 microns thick. In a preferred embodiment, the metal layer is titanium.

Biocompatible polymer coatings, include parylene, polyimides, silicones, epoxies, liquid crystal polymers, polyethylene glycols, polyethylene terephthalates, tetrafluoroethylenes or suitable mixtures, copolymers of block polymers thereof. Again, techniques for depositing polymer coatings are well known and include dipping, spraying, spin coating, chemical vapor deposition ("CVD"), etc. According to an aspect of the present invention, the thin polymer layer is preferably between about 3 and about 15 microns thick, and is more preferably between about 4 and about 10 microns thick.

Figure 3:
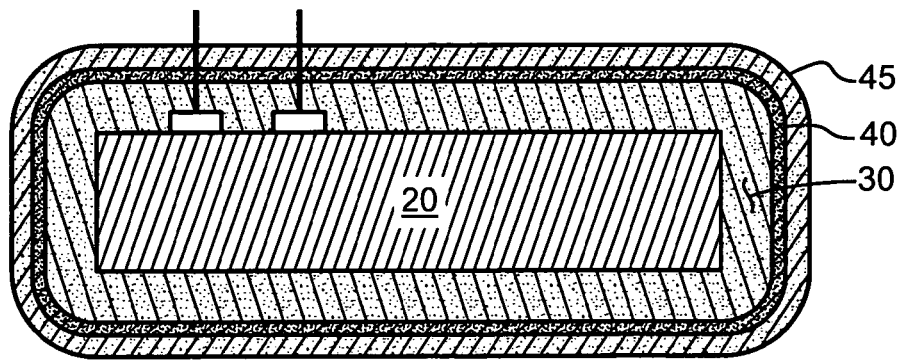
FIG. 3 is a cross-sectional drawing of an implantable micro-miniature device in accordance with a second embodiment of the present invention.

As noted, according to the present invention, coating 40 extends the life of the insulating layer 30 by preventing or slowing any reactions that may degrade the layer 30. In the case where more than one reaction is possible, a plurality of coatings 40 may be beneficial, as each coating may serve to retard a single process, and so collectively the plurality of coating extends the lifetime beyond that of any coating used individually. FIG. 3 shows an implantable device 310 in accordance with another embodiment of the present invention, having a first polymer or metal layer 40 and a second polymer or metal layer 45 overlying hermetic insulating layer 30.

FIG. 4 is a table showing the results of testing of coatings conducted by the inventors. Four micron alumina coatings were coated with 5 to 15 um of parylene C, a biocompatible polymer. Samples with and without the parylene coating were soaked in phosphate buffered solution at first at 57° C. for 40 days and then at 77° C. and monitored for degradation. Energy dispersive X-ray analysis revealed that the alumina coating (stopped after 120 days at 77° C.) were completely eroded away in about 6 months (corresponding to an estimated exposure in living tissue of more than 5 years), while the parylene coated samples show no signs of degradation after 7 months, corresponding to an estimated exposure in living tissue at body temperature of more than 8 years.

FIG. 4 presents the test results for passive soaking in a phosphate buffered saline solution at 57° C. Area I is at the interface of the partially submerged test article. Area II is the submerged portion and Area III is the portion of the test article that is above the interface. Samples 1, 2, and 3 were completely submerged while samples 4, 5, and 6 were partially submerged for the time listed in Table 1 (FIG. 4).

The testing shows that there was accelerated alumina coating dissolution at the liquid-air interface. The eight micron parylene secondary coating (applied by vacuum vapor deposition), protected and slowed the dissolution of the IBAD alumina insulating coating. It was observed by scanning electron microscopy that where a pin hole existed in the parylene, that the alumina disappeared in the nearby area.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A micro-miniature implantable device comprising:
   a device for use within a living organism, a contact pad on said device connected to a conductor;

a biocompatible inorganic hermetic insulating conformal coating deposited directly on said device for use within a living organism and defining an opening over said contact pad, wherein the biocompatible inorganic hermetic insulating conformal coating surrounds the device for use within a living organism, and a biocompatible protective polymer conformal layer directly overlying said biocompatible inorganic hermetic insulating conformal coating and defining an opening over said contact pad;

wherein the conductor extends through the inorganic hermetic insulated coating and the biocompatible protective polymer conformal layer.

2. The micro-miniature implantable device of claim 1, wherein said device for use within a living organism comprises an active electronic circuit.

3. The micro-miniature implantable device of claim 2, wherein said device for use within a living organism comprises an integrated circuit chip, and said biocompatible inorganic hermetic insulating conformal coating covers at least a portion of said integrated circuit chip.

4. The micro-miniature implantable device of claim 1 wherein said device for use within a living organism comprises a passive component.

5. The micro-miniature implantable device of claim 4 wherein said passive component is a resistor, inductor, capacitor, or magnet.

6. The micro-miniature implantable device of claim 1, wherein said biocompatible inorganic hermetic insulating conformal coating is a biocompatible ceramic coating.

7. The micro-miniature implantable device of claim 1, wherein said biocompatible inorganic hermetic insulating conformal coating comprises a biocompatible metal oxide coating.

8. The micro-miniature implantable device of claim 7, wherein said biocompatible metal oxide coating comprises aluminum oxide, zirconium oxide, titanium dioxide, vanadium oxide, or mixtures thereof.

9. The micro-miniature implantable device of claim 1, wherein said biocompatible inorganic hermetic insulating conformal coating comprises silicon carbide, titanium nitride, aluminum nitride, silicon nitride, silicon dioxide, ultra-nano crystalline diamond, or mixtures thereof.

10. The micro-miniature implantable device of claim 1, wherein said biocompatible protective polymer conformal layer comprises parylene.

11. The micro-miniature implantable device of claim 1, wherein said biocompatible protective polymer conformal layer comprises a polyimide, a silicone, an epoxy, a liquid crystal polymer, a polyethylene glycol, a polyethylene terephthalate, a tetrafluoroethylene, or mixtures, copolymers, or block polymers thereof.

12. The micro-miniature implantable device of claim 1 wherein said biocompatible inorganic hermetic insulating conformal coating has a thickness less than about 10 micrometers.

13. The micro-miniature implantable device of claim 1 wherein said biocompatible protective polymer conformal layer has a thickness less than about 15 micrometers.

14. The micro-miniature implantable device of claim 13 wherein said biocompatible protective polymer conformal layer has a thickness between about 3 and about 15 micrometers.

15. The micro-miniature implantable device of claim 13 wherein said biocompatible protective polymer conformal layer has a thickness between about 4and about 10 micrometers.

16. The micro-miniature implantable device of claim 1 further comprising at least one biocompatible protective layer overlying said biocompatible protective polymer conformal layer.

17. A micro-miniature implantable device, comprising:
a device for use within a living organism, said device for use within a living organism comprising an active electronic circuit;

a contact pad on said device connected to a conductor;

a biocompatible inorganic hermetic insulating conformal coating deposited directly on and surrounding said device for use within a living organism and defining an opening over said contact pad, wherein the biocompatible inorganic hermetic insulating conformal coating form a compete hermetic encasement of the device for use within a living organism; and a biocompatible protective metal conformal layer directly overlying and substantially covering said biocompatible inorganic hermetic insulating conformal coating and defining an opening over said contact pad;

wherein the conductor extends through the inorganic hermetic insulated conformal coating and the biocompatible protective metal conformal layer.

18. The micro-miniature implantable device of claim 17, wherein said biocompatible protective metal conformal layer comprises titanium, platinum, iridium, or mixtures thereof.

19. The micro-miniature implantable device of claim 17, wherein said biocompatible protective metal conformal layer comprises titanium.

20. The micro-miniature implantable device of claim 17, wherein said biocompatible protective metal conformal layer is between about 0.01 and about 10 micrometers thick.

21. The micro-miniature device of claim 17, wherein said biocompatible protective metal conformal layer is between about 0.02 and about 8 micrometers thick.

22. The micro-miniature implantable device of claim 17, wherein said biocompatible protective metal conformal layer is between about 0.03 and about 6 micrometers thick.

23. The micro-miniature implantable device of claim 17 further comprising at least one biocompatible protective layer overlying said biocompatible protective metal conformal layer.

* * * * *